United States Patent [19]

Greb et al.

[11] 4,368,870
[45] Jan. 18, 1983

[54] MOLDING ASSEMBLY FOR PLASTIC DECORATIONS

[75] Inventors: Gregory A. Greb, Melrose Park; Raymond W. Spitza, Northlake; Robert R. Moe, La Grange, all of Ill.

[73] Assignee: Alberto-Culver Company, Melrose Park, Ill.

[21] Appl. No.: 296,579

[22] Filed: Aug. 31, 1981

[51] Int. Cl.³ ............................. B29C 1/00; B29C 5/00
[52] U.S. Cl. .................................. 249/102; 249/104; 249/139; 249/155; 425/183
[58] Field of Search ............... 249/102, 104, 139, 155; 425/183

[56] References Cited

U.S. PATENT DOCUMENTS

| 1,092,195 | 4/1914 | Workman | 249/102 X |
| 2,330,989 | 10/1943 | Nevills | 425/119 |
| 2,460,832 | 2/1949 | La Follette | 425/119 X |
| 2,689,375 | 9/1954 | Hugger | 425/119 |
| 3,128,724 | 4/1964 | Linder | 249/102 |
| 3,179,980 | 4/1965 | Ryan et al. | 249/102 X |

*Primary Examiner*—J. Howard Flint, Jr.

[57] ABSTRACT

An assembly is provided for molding plastic decorations. The assembly includes a support plate for the mold frame and holding fixtures which are positionable to provide a snap-in and snap-out holding relation with the mold frame. The assembly is adapted for use in manufacturing perfume-release plastic decorations which resemble stained glass miniatures.

8 Claims, 3 Drawing Figures

MOLDING ASSEMBLY FOR PLASTIC DECORATIONS

RELATED APPLICATION

This application is related to the application filed on even date herewith, entitled "Perfume-Release Plastic Decorations And Method Of Manufacturing", Ser. No. 296,580. More specifically, the molding assembly comprising the invention of this application can advantageously be employed in the manufacturing of perfume-release plastic decorations by the method of the cited co-pending application.

BACKGROUND AND PRIOR ART

The general field of this invention relates to the molding of plastic decorations which resemble stained glass miniatures, particularly decorations of this kind which are formed from thermoplastic compositions containing a volatile perfume for release into the atmosphere when the plastic decorations are displayed in a room. No directly relevant prior art reference are known. However, thermoplastic compositions containing volatile components for release in the atmosphere are described in a number of U.S. Patents, including U.S. Pat. Nos. 3,725,311, 3,926,655, 4,051,159, 4,095,031, and 4,184,099. These United States Patents do not particularly describe the insertion of such thermoplastic compositions in frames defining the shape and providing support for the formed resins. In published South African Specification No. 770,610, a stained glass mobile is described which is formed from a metal frame and a hydrophilic thermo-setting resin composition containing a perfume oil (see Example IX). Neither this reference nor any other known prior art reference describes an assembly for holding frames providing openings therethrough and closed by ribs for receiving and retaining liquified thermoplastic compositions.

THE DRAWINGS

The molding assembly of this invention is illustrated in a preferred embodiment in the accompanying drawing in which.

DETAILED DESCRIPTION

Figure 1:
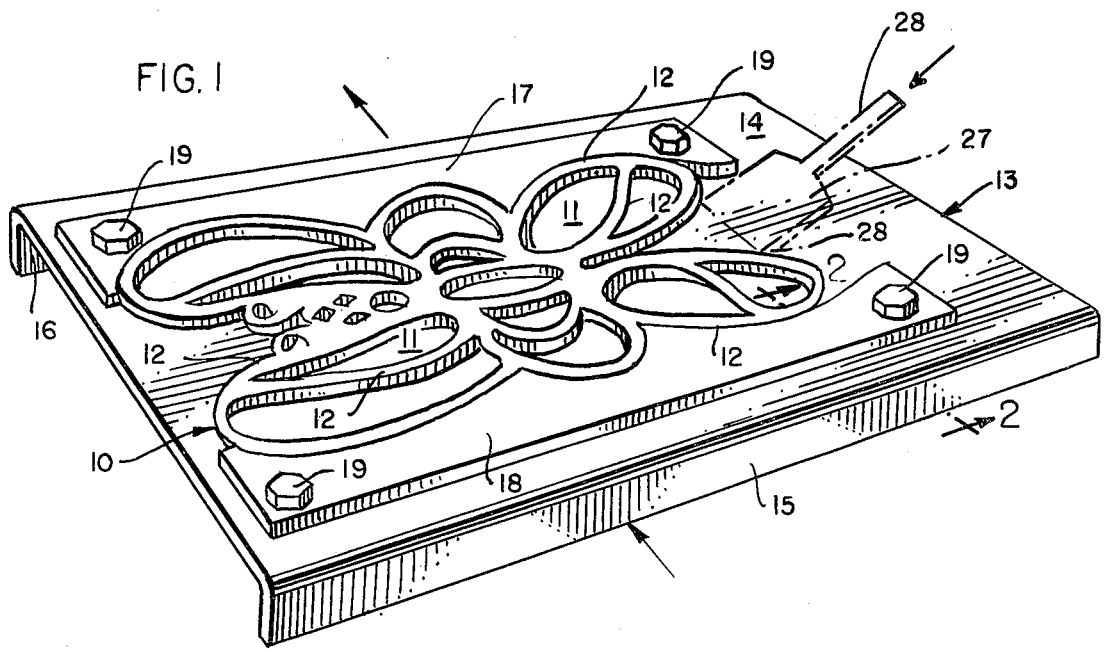
FIG. 1 is a perspective view of the complete assembly including the support plate, a mold frame in the shape of a butterfly, and a pair of holding fixtures arranged on each side of the frame.

Looking first at FIG. 1, there is showed an assembly for molding plastic decorations resembling stained glass miniatures. In the illustration given, the frame designated generally by the number 10 is in the shape of a butterfly. It will be understood that a variety of frame shapes and configurations can be used, and it is one of the advantages of the assembly of the present invention that it can be adapted for use with frames of any configuration or shape. In general, as illustrated in FIG. 1, the frames 10, as used in the assembly, are flat shallow horizontally-extending frames which provide at least one and preferably a plurality of openings therethrough, such as the openings 11 of the butterfly frame shown, a plurality of openings 11 of different sizes and shapes being provided. The openings 11 are enclosed by thin ribs 12 which enclose the openings for receiving and retaining liquified thermoplastic compositions. Usable thermoplastic compositions and the method of filling the frame with such compositions are descibed in the co-pending application filed on even date herewith, entitled "Perfume-Release Plastic Decorations And Method of Manufacturing".

As shown in FIG. 1, the mold frame 10 is positioned on the upper surface of a support plate 13. In the illustration given, plate 13 has a horizontally-extending central portion 14 connected to downwardly-extending side flanges 15 and 16. The side flanges can be employed for hingedly connecting the plates in a series to provide an endless conveyor, which is utilized in manufacturing apparatus having heating and cooling means below the conveyor plates, such as means for preheating the plates before the frames are filled, and means for cooling the plates and the frames after they are filled. For these purposes, it is preferable to form the plates 13 from a heat conductive metal such as aluminum or steel. Further, since the upper surface of the plates will act as mold surfaces to close the bottoms of the frame openings 11, it is preferred to have the plate upper surfaces provided with a mold release layer. For example, the plates may be coated with Teflon or Mylar sheets may be adhesively attached to the metal surfaces of the plates. In a particularly desirable construction, thin sheets of a release material are removably attached to the plates. For example, Teflon impregnated fiberglass sheets can be used. Such sheet material in the form of tape rolls are available from manufacturers in the United States, such as Taconic Plastics, Inc., Petersburg, N.Y., and Dodge Fluorglass Division, Oak Materials Group, Inc., Hoosic Falls, N.Y. The pressure-sensitive adhesive on such tapes should be selected to be resistant to the temperatures up to the highest temperatures encountered in molding the plastic decorations. Such sheet material can be removed and replaced as required to recondition the plates for further use in the process.

In accordance with the present invention, frame holding fixtures are provided which securely retain the mold frames on the plates 13 during processing, while permitting the frames to be inserted and removed, respectively, by a snap-in and snap-out arrangement.

As shown in FIG. 1, the pair of holding fixtures as designated generally by the numbers 17 and 18. As shown, the fixtures 17, 18, respectively, extend along oppositely-disposed sides of frame 10 and are arranged to engage outer rib portions thereof. The relationship of the fixture 18 to the outer rib 12 is shown more clearly in FIG. 2. The frame rests on the release layer 13a of the support plate 13 and is held thereon between the fixtures 17 and 18, the relationship of the fixture 17 to the facing rib 12 of the frame being the same as that shown in FIG. 2.

The fixtures 17, 18 which may be in the form of flat elongated strips, as shown, are adjustably bolted to the plates 13. For example, as shown, the attachment bolts 19 may have shanks 20 extending through oversized holes 21 in the fixtures, such as fixture 18, the shanks 20 terminating in threaded extensions 22 which are received in threaded openings 23 of the plate 13. When the bolts 19 are loosened, this permits the fixture strips 17, 18 to be adjusted with respect to their position on the plate so that they snuggly receive and engage the outer rib portions of the frame 10.

Figure 2:
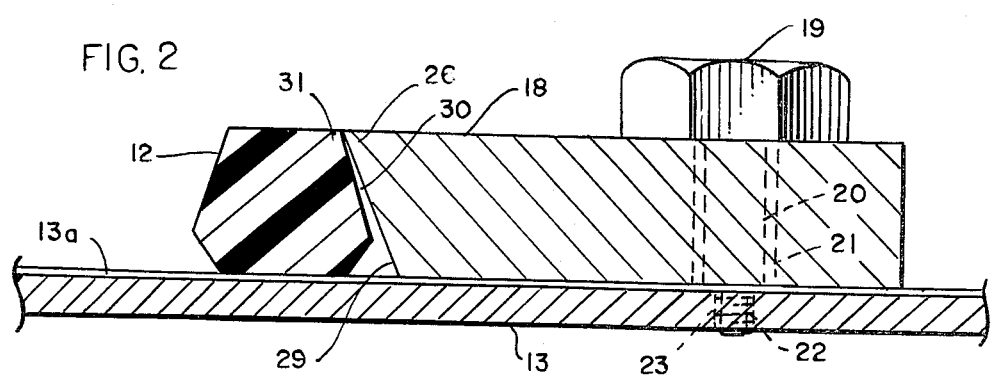
FIG. 2 is an enlarged detail sectional view taken on line 2—2 of FIG. 2 showing the relation of one of the hold-down fixtures to the outer rib portion of the mold frame.

An advantageous relation of the inserted outer frame rib 12 and holding fixture 18 is shown in FIG. 2. The fixtures, such as fixture 18, provide inner edge portions which conform longitudinally (see FIG. 1) to the configuration of the outer ribs, and which also are shaped to releasably engage the facing sides of the frame rib portions (see FIG. 2). In accordance with the present invention, this engagement provides a snap-in and snap-out relation between the frame 10 and the holding fixtures 17, 18.

Figure 3:
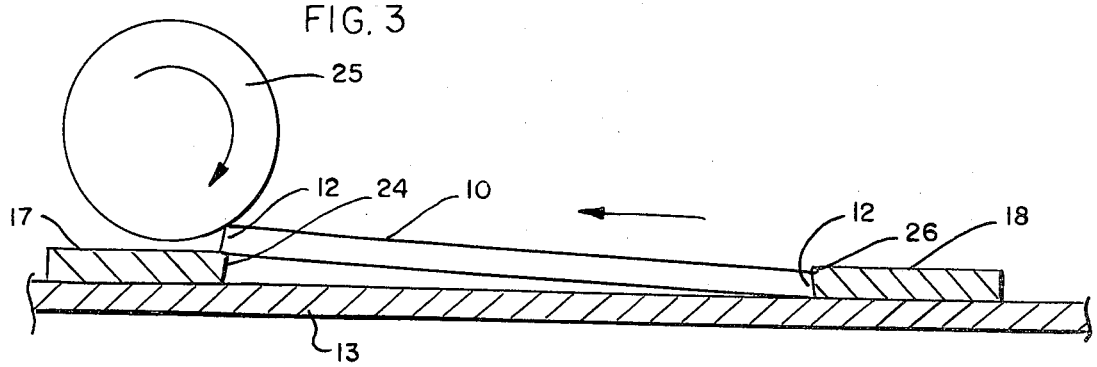
FIG. 3 is a diagramatic elevational view illustrating how a frame may be inserted in the holding fixture of FIGS. 1 and 2 by a snap-in type action.

In FIG. 3, the desired snap-in action is illustrated. Assuming, for example, that the plate 13 is part of a conveyor system traveling in the direction indicated by the two aligned arrows in FIG. 1, the fixture 17 will be on the forwardly moving side of the plate and the fixture 18 on the rearward side. The frame 10 may then be manually inserted with the outer rearward rib portion 12 seated within and in engagement with the inner edge portion of the fixture 18. The forward outer rib portion 12 will then be resting on the upper corner 24 of the fixture 17. By providing a pressor roller 25 in the path of forward movement of the plate and frame assembly, as shown in FIG. 3, the roller will engage the forward rib portion 12 and will snap it into engagement with the inner edge portion of the fixture 17, as shown in FIG. 1.

After insertion, the upper corners respectively, 24 and 26 of fixtures 17 and 18 will act to hold the frame 10 in position, while permitting it to be easily released by a snap-out type action. For example, as illustrated in dotted lines in FIG. 1, the frame 10 can be removed by the insertion of a blade 27 which has a tapered forward edge 28 for slipping between the frame 10 and the upper surface of the plate 13. For example, the blade 27 may be attached to a hydraulically actuated rod 28, which can provide means for automatically removing the frames.

As described in the above-cited co-pending application, entitled "Perfume-Release Plastic Decorations and Method Of Manufacturing", the frames may be removed by a snap-out type action, as described above, with the plates 13 in an inverted condition. For example, if the plates form a continuous endless conveyor, the frames 12 may be removed from the bottom or return portion of the conveyor. When the frames are snapped out in this manner by using an insertion blade, such as the blade 27 described above, they can fall downwardly onto a conveyor, which will move the frames to a heat treatment unit for further processing of the sides of the filled frames which were in contact with the upper surfaces of the plates 13. Since these surfaces will be somewhat irregular, the surface of the filled plastic compositions in contact therewith will have similar irregularities, and this can detract from the clarity and light-transmitting appearance of the decorations. As described in the cited co-pending application, however, these surfaces can easily be clarified by heat treatment which liquifies a thin layer of the marred surfaces. It is therefore a desirable feature of the holding assembly of the present invention that the frames can easily be removed on a continuous mechanical basis for such further processing.

Returning now to the illustration of FIG. 2, as shown, the holding fixture 18 provides surface 29 along its inner edge portion, which in cross-section inclines upwardly and inwardly for releasably engaging the facing side 30 of the frame rib 12. The opposed surface 30 of the frame rib is provided with a downward and outward inclination at a similar angle to that of the fixture surface 29. The inclination of surfaces may be identical, or, as shown, the fixture surface 29 may have a slightly greater inclination with respect to the vertical than the rib surface 30, such as an inclination of about 0.5° to 1° greater. The surfaces 29, 30 will then engage substantially along their length or, as shown, the engagement will be primarily at their upper corners. In the illustration given, the fixture corner 26 bears against the upper corner 31 of the frame rib. This engagement is not such, however, as to compress the frame transversely after insertion. The frames are preferably formed of a relatively rigid material, but because of their open structure, they will be slightly compressable, which can facilitate the snap-in insertion and snap-out removal. For example, the frames may be formed of a temperature-resistant plastic, such as a thermosetting resin or thermoplastic resin having a softening temperature appreciably above the processing temperatures to be used in filling the frames. A temperature-resistant thermoplastic material is particularly desirable since it facilitates the molding of the frames with the ribs in the desired configuration to produce a particular design, such as the butterfly design shown in FIG. 1. For example, the frames may be formed of polyethylene terephthalate which may be reinforced, such as with glass fibers. A commercial material of this kind is sold under the name "Ryanite" by E. I. duPont.

In the foregoing description, details have been set out for purpose of illustration and specific preferred embodiments have been described. However, it will be apparent to those skilled in the art that many of the details described are not critical features of the invention, and that other embodiments can be made without departing from the basic principles of the invention.

We claim:

1. An assembly for molding plastic decorations resembling stained glass miniatures, comprising:
   a. a horizontally-extending support plate;
   b. a flat shallow horizontally-extending frame positioned on the upper surface of said plate, said frame providing at least one opening therethrough enclosed of its sides by ribs of said frame for receiving and retaining liquified thermoplastic composition; and
   c. a pair of holding fixtures extending along oppositely-disposed sides of said frame and engaging outer rib portions thereof, said fixtures being adjustably secured to said plate so that they can be precisely positioned on said plate in relation to said frame outer ribs portions, said fixtures providing inner edge portions conforming to the shape of said outer rib portions, said fixtures inner edge portions releasably engaging the facing sides of said frame rib portions, said engagement providing a snap-in and snap-out relation between said frame and said holding fixtures.

2. The assembly of claim 1 in which said plate is formed of a heat-conductive metal and has an upper surface with a mold release layer thereon in contact with said frame.

3. The assembly of claim 1 in which said frames provides a plurality of openings therethrough enclosed on their sides by said frame ribs.

4. The assembly of claim 1 in which said fixture facing sides of said frame outer rib portions have side portions providing a downward and outward inclination at a similar angle to that of said frame inner edge portions which provide said snap-in and snap-out engagement.

5. The assembly of claim 1 in which said fixtures are in the form of flat elongated strips which are removably attached to said plate so that said strips can be replaced when said plate is to be used with a different frame.

6. An assembly for molding plastic decorations resembling stained glass miniatures, comprising:
  a. a horizontally-extending support plate formed of a heat-conductive metal, said plate having an upper surface with a mold release layer thereon;
  b. a flat shallow horizontally-extending frame positioned on the upper surface of said plate, said frame providing a plurality of separate openings therethrough enclosed on their sides by ribs of said frame for receiving and retaining liquified thermoplastic compositions; and
  c. a pair of holding fixtures extending along oppositely-disposed sides of said frame engaging outer rib portions thereof, said fixtures being adjustably secured to said plate so that they can be precisely positioned on said plate in relation to said frame outer rib portions, said fixtures providing inner edge portions conforming to the shape of said outer rib portions, said inner edge portions of said fixtures having an inward and upward inclination for releasably engaging the facing sides of said frame rib portions, said engagement providing a snap-in and snap-out relation between said frame and said holding fixtures, 7. The assembly of claim 6 in which said fixture facing sides of said frame outer rib portions have side portions providing a downward and outward inclination at a similar angle to that of said frame inner edge portions which provide said snap-in and snap-out engagement.

8. The assembly of claim 6 in which said fixtures are in the form of flat elongated strips which are removably attached to said plate so that said strips can be replaced when said plate is to be used with a different frame.

* * * * *